United States Patent
Nishinaga et al.

(10) Patent No.: US 9,598,715 B2
(45) Date of Patent: Mar. 21, 2017

(54) METHOD FOR MEASURING COLOR CHANGE OF OXIDATION-REDUCTION INDICATOR

(75) Inventors: Eiji Nishinaga, Tokyo (JP); Naho Suzuki, Tokyo (JP); Takashi Hama, Kyoto (JP); Isao Fukuta, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 180 days.

(21) Appl. No.: 14/348,199

(22) PCT Filed: Aug. 17, 2012

(86) PCT No.: PCT/JP2012/070903
§ 371 (c)(1),
(2), (4) Date: May 13, 2014

(87) PCT Pub. No.: WO2013/046995
PCT Pub. Date: Apr. 4, 2013

(65) Prior Publication Data
US 2014/0322749 A1    Oct. 30, 2014

(30) Foreign Application Priority Data

Sep. 30, 2011 (JP) ................................. 2011-217921

(51) Int. Cl.
*C12Q 1/14* (2006.01)
*C12Q 1/04* (2006.01)
*C12Q 1/06* (2006.01)
*C12Q 1/32* (2006.01)
*G01N 33/52* (2006.01)

(52) U.S. Cl.
CPC .................. *C12Q 1/14* (2013.01); *C12Q 1/04* (2013.01); *C12Q 1/06* (2013.01); *C12Q 1/32* (2013.01); *G01N 33/52* (2013.01); *G01N 2333/9029* (2013.01)

(58) Field of Classification Search
CPC ... C12Q 1/04; C12Q 1/32; C12Q 1/14; C12Q 1/06; G01N 2333/9029; G01N 33/52
See application file for complete search history.

(56) References Cited

U.S. PATENT DOCUMENTS

| | | | |
|---|---|---|---|
| 3,741,876 A | 6/1973 | Guilbault et al. | |
| 4,582,795 A | 4/1986 | Shibuya et al. | |
| 5,354,658 A * | 10/1994 | Wright | C12Q 1/34 435/21 |
| 2010/0270151 A1 | 10/2010 | Cardosi et al. | |
| 2011/0008748 A1 * | 1/2011 | Haeberlein | C12Q 1/04 433/83 |

FOREIGN PATENT DOCUMENTS

| | | | |
|---|---|---|---|
| EP | 2660597 A1 | 11/2013 | |
| FI | EP 0496409 A1 * | 7/1992 | ............... C12Q 1/04 |
| JP | 58-225029 A | 12/1983 | |
| JP | 62-239999 A | 10/1987 | |
| JP | 10-210998 A | 8/1998 | |
| JP | 2004-093335 A | 3/2004 | |
| JP | 2004-219309 A | 8/2004 | |
| JP | 2004-233289 A | 8/2004 | |
| JP | 2010-256357 A | 11/2010 | |
| JP | 2011-502129 A | 1/2011 | |
| WO | 00/65066 A1 | 11/2000 | |

OTHER PUBLICATIONS

Tominaga H. et al., "A water-soluble tetrazolium salt useful for colorimetric cell viability assay", Anal. Commun., 1999, vol. 36, pp. 47-50.*
Niles A.L. et al., "Update on in vitro cytotoxicity assays for drug development", Expert Opin. Drug Discovery, 2008, vol. 3, No. 6, pp. 655-669.*
Porter E.V. et al., "Partial purification and properties of a mannofructokinase from *Streptococcus mutans* SL-1", Infection and Immunity, 1980, vol. 30, No. 1, pp. 43-50.*
International Preliminary Report on Patentability and Written Opinion issued in corresponding International Patent Application No. PCT/JP2012/070903 dated Apr. 10, 2014.
International Search Report issued in corresponding International Patent Application No. PCT/JP2012/070903 dated Sep. 11, 2012.
Extended European Search Report issued in corresponding European Patent Application No. 12835784.5 dated Mar. 17, 2015.
Castillo et al., "Fluorometric Cyclic Assays for Pyridine Nucleotides Reduced or Oxidized in Enzyme-Coupled Assays," Microchemical Journal, 38: 191-205 (1988).
Li et al., "Immobilized enzymatic fluorescence capillary biosensor for determination of sulfated bile acid in urine," Biosensors and Bioelectronics, 24: 538-544 (2008).
Lendzian et al., "Regulation of Glucose-6-Phosphate Dehydrogenase in Spinach Chloroplasts by Ribulose 1,5-Diphosphate and NADPH/NADP+ Ratios," Biochimica et Biophysica Acta, 396: 260-275 (1975).
Office Action issued in corresponding Japanese Patent Application No. 2013-536067 dated Aug. 9, 2016.
Held, "An Absorbance-based Cytotoxicity Assay using High Absorptivity, Water-soluble Tetrazolium Salts," BioTek Application Note, Mar. 20, 2009 (http://www.biotek.jp/ja/resources/articles/cytotoxicity-assay.html).

* cited by examiner

*Primary Examiner* — Saytendra K Singh
(74) *Attorney, Agent, or Firm* — Morgan, Lewis & Bockius LLP

(57) ABSTRACT

Provided is a method for measuring a color change of an oxidation-reduction indicator, which method is applicable to measurement of the cariogenic bacterial count and the like. A color change of an oxidation-reduction indicator is measured by a method for measuring a color change of an oxidation-reduction indicator, the method comprising reacting a test reagent with a test sample and measuring a color change, wherein the test reagent contains an oxidation-reduction indicator, an oxidation-reduction promoter, and a halogen salt.

2 Claims, 4 Drawing Sheets

(A)

(B)

METHOD FOR MEASURING COLOR CHANGE OF OXIDATION-REDUCTION INDICATOR

TECHNICAL FIELD

The present invention relates to a method for measuring a color change of an oxidation-reduction indicator, which method is applicable to measurement of the cariogenic bacterial count and the like, and a test piece to be used therefor.

BACKGROUND ART

Various bacteria are present in the oral cavity, and those that cause caries are called cariogenic bacteria. For example, it is thought that a high cariogenic bacterial count in saliva indicates that the caries risk, i.e. a risk that indicates to what extent the conditions of the oral cavity are likely to cause caries, is high. Known examples of the method for detecting cariogenic bacteria include detection methods using resazurin, which is an oxidation-reduction indicator (Patent Documents 1 and 2), and detection methods utilizing chemiluminescence based on a reducing power such as NADH (Patent Document 3).

Resazurin is usually present as resazurin, which is an oxidized blue pigment (maximum absorption wavelength, 605 nm), but it is reduced by NADH or NADPH (these may be hereinafter collectively referred to as "NAD(P)H") produced as a result of bacterial metabolism to be converted into resorufin, which is a reddish purple pigment (maximum absorption wavelength, 573 nm). Resorufin is further reduced by NAD(P)H to be converted into hydroresazurin, which is colorless. Therefore, a color change of resazurin allows measurement of the number of bacteria, mainly gram-positive bacteria including cariogenic bacteria, in a test substance. Known examples of measurement systems for the cariogenic bacterial count utilizing resazurin include RD test "Showa" (trade name; Showa Yakuhin Kako Co., Ltd.) and CAT21 Fast (trade name; Willdent Co., Ltd.).

Electron carriers such as 1-methoxy-5-methylphenazinium methyl sulfate (1-methoxy PMS), phenazinium methyl sulfate (PMS), and phenazine ethosulfate (PES) are used, for example, reaction systems using a tetrazolium salt as a color reagent, as a mediator for oxidation-reduction reaction of the tetrazolium salt. Although it is said that PMS can be used as a mediator in reaction systems using resazurin as an oxidation-reduction indicator (Patent Document 4), diaphorase is said to be more preferred than PMS as the mediator (Patent Document 4).

However, use of a salt such as sodium chloride or potassium chloride in such reaction systems using an oxidation-reduction indicator and a mediator has not been known.

PRIOR ART DOCUMENTS

Patent Documents

[Patent Document 1] JP 58-225029 A
[Patent Document 2] JP 2004-093335 A
[Patent Document 3] JP 10-210998 A
[Patent Document 4] JP 62-239999 A

SUMMARY OF THE INVENTION

Problems to be Solved by the Invention

Since the above-described conventional measurement systems for the cariogenic bacterial count require a controlled temperature of 32° C. to 37° C. and a reaction time of 15 to 20 minutes, measurement of the cariogenic bacterial count in a dental clinic or the like in a short time has been impossible. Further, in cases where the temperature is not controlled, the time required for the reaction further increases, which is problematic. That is, the conventional measuring methods for the cariogenic bacterial count still need to be improved from the viewpoints of the reaction temperature and the required time. The present invention aims to provide a novel method for measuring a color change of oxidation-reduction indicators, which method is applicable to measurement of the cariogenic bacterial count and the like.

Means for Solving the Problems

As a result of intensive study, the present inventors discovered that, in measurement methods for the cariogenic bacterial count using a test reagent containing resazurin as a color indicator, the color reactivity could be increased by addition of 1-methoxy-5-methylphenazinium methyl sulfate (1-methoxy PMS) as a component of the test reagent. The present inventors discovered that the color reactivity could be further increased by further addition of sodium chloride, potassium chloride, sodium bromide or potassium bromide as a component of the test reagent, thereby completing the present invention.

That is, the present invention can be exemplified as follows.

[1]
A method for measuring a color change of an oxidation-reduction indicator, the method comprising:
reacting a test reagent with a test sample and measuring a color change,
wherein the test reagent contains an oxidation-reduction indicator, an oxidation-reduction promoter, and a halogen salt.

[2]
The method according to [1], which is a method for measuring the cariogenic bacterial count in the test sample.

[3]
The method according to [1] or [2], wherein the oxidation-reduction indicator is resazurin.

[4]
The method according to any one of [1] to [3], wherein the oxidation-reduction promoter is 1-methoxy-5-methylphenazinium methyl sulfate, phenazinium methyl sulfate, or phenazine ethosulfate.

[5]
The method according to any one of [1] to [4], wherein the halogen salt is sodium chloride, potassium chloride, sodium bromide, or potassium bromide.

[6]
The method according to any one of [1] to [5], wherein the measurement is carried out using a test piece comprising a support carrier and an absorption carrier carried by the support carrier, wherein the absorption carrier holds the test reagent.

[7]
A reagent for measuring NADH and NADPH, the reagent comprising an oxidation-reduction indicator, an oxidation-reduction promoter, and a halogen salt.

[8]
The reagent according to [7], wherein the oxidation-reduction indicator is resazurin.

[9]

The reagent according to [7] or [8], wherein the oxidation-reduction promoter is 1-methoxy-5-methylphenazinium methyl sulfate, phenazinium methyl sulfate, or phenazine ethosulfate.

[10]

The reagent according to any one of [7] to [9], wherein the halogen salt is sodium chloride, potassium chloride, sodium bromide, or potassium bromide.

[11]

A test piece for use in measurement of NADH and NADPH, the test piece comprising a support carrier and an absorption carrier carried by the support carrier, wherein the absorption carrier holds the reagent according to any one of [7] to [10].

[12]

The test piece according to [11], which is a test piece for use in measurement of the cariogenic bacterial count.

Effect of the Invention

By the present invention, a color change of an oxidation-reduction indicator can be clearly measured. Thus, by the present invention, the cariogenic bacterial count can be measured at room temperature in a short time. Therefore, by the present invention, in clinical sites such as dental clinics, many samples can be processed without use of facilities such as an incubator, and the cariogenic bacterial count can be tested simply and rapidly.

MODE FOR CARRYING OUT THE INVENTION

Figure 1:
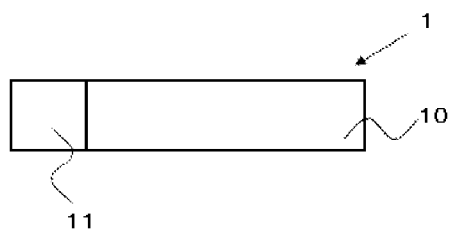
FIG. 1(A) is a plan view illustrating an embodiment of the test piece of the present invention.
FIG. 1(B) is a front view illustrating an embodiment of the test piece of the present invention.
Figure 1:
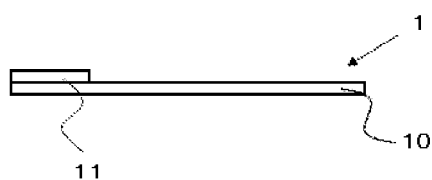

The present invention is described below in detail.

The method of the present invention is a method for measuring the coloration of an oxidation-reduction indicator, wherein an oxidation-reduction indicator, an oxidation-reduction promoter, and a halogen salt are used.

That is, the method of the present invention is a method for measuring a color change of an oxidation-reduction indicator, the method comprising reacting a test reagent with a test sample and measuring a color change, wherein the test reagent contains an oxidation-reduction indicator, an oxidation-reduction promoter, and a halogen salt.

In the method of the present invention, the oxidation-reduction indicator is an indicator whose color changes due to an oxidation-reduction reaction using NAD(P)H as an electron donor. Therefore, the test reagent can be used as a reagent for measuring NAD(P)H.

Similarly, the method of the present invention can be used for detection of NAD(P)H contained in a test sample and/or NAD(P)H produced in a reaction system. Therefore, for example, by the method of the present invention, NAD(P)H produced as a result of metabolism in bacteria contained in a test sample can be detected, and this then allows detection of the bacteria contained in the test sample. Specific examples of such bacteria include cariogenic bacteria.

That is, an embodiment of the present invention is a method for measuring the cariogenic bacterial count in a test sample, the method comprising reacting a test reagent with a test sample and measuring a color change, wherein the test reagent contains an oxidation-reduction indicator, an oxidation-reduction promoter, and a halogen salt. The method of the present invention is described below by way of example of the method for measuring the cariogenic bacterial count. It should be noted that the oxidation-reduction indicator, oxidation-reduction promoter, and halogen salt may be collectively referred to as the "effective components".

In the present invention, cariogenic bacteria refer to causative bacteria of caries. Specific examples of the cariogenic bacteria include *Streptococcus mutans* and *Streptococcus sobrinus*. It is thought that, as the cariogenic bacterial count increases, the caries risk, i.e. the risk of developing caries, increases.

In the present invention, the test sample to be subjected to measurement of the cariogenic bacterial count is not limited. Examples of the test sample to be subjected to measurement of the cariogenic bacterial count include test samples obtained from the oral cavity. Examples of the test samples obtained from the oral cavity include resting saliva (unstimulated saliva), stimulated saliva, and mouth wash solution. Examples of the stimulated saliva include saliva collected by stimulation with chewing gum. Among these, mouth wash solution is preferred. Mouth wash solution can be obtained by, for example, placing purified water in the mouth and then expectorating it. More specifically, for example, 3 mL of purified water is held in the mouth for 10 seconds and then expectorated into a container. The volume of the purified water and the length of time of holding the purified water in the mouth may be appropriately changed as required. The obtained test sample may be used for the subsequent operations without any special pretreatment, but, as required, an additional operation such as dilution may be carried out. Examples of the test sample to be subjected to measurement of the cariogenic bacterial count also include samples containing cariogenic bacteria, such as cultures of cariogenic bacteria. The culture of cariogenic bacteria may be, for example, a culture of an isolated cariogenic bacterial strain that is available from a bioresource bank such as ATCC.

In the present invention, the test reagent contains an oxidation-reduction indicator. In the present invention, the oxidation-reduction indicator is not limited as long as it is an indicator whose color changes due to oxidation-reduction reaction using NAD(P)H as an electron donor. NAD(P)H is generated by bacterial metabolism. That is, reduction of the oxidation-reduction indicator proceeds depending on the number of bacteria, mainly on the number of living gram-positive bacteria including cariogenic bacteria, contained in the test sample. Therefore, a color change due to reduction of the oxidation-reduction indicator reflects the cariogenic bacterial count. The term "using NAD(P)H as an electron donor" means either direct reduction by NAD(P)H or indirect reduction via another substance (mediator) that is reduced by NAD(P)H. Specific examples of the oxidation-reduction indicator include resazurin, tetrazolium salts, methylene blue, and xylene blue. Among these, resazurin is preferred. Each of these may be contained alone, or an arbitrary combination of these may be contained.

Resazurin is usually present as resazurin, which is an oxidized blue pigment (maximum absorption wavelength, 605 nm), but it is reduced by NAD(P)H to be converted into resorufin, which is a reddish purple pigment (maximum absorption wavelength, 573 nm). Resorufin is further reduced by NAD(P)H to be converted into hydroresazurin, which is colorless.

Tetrazolium salts are reduced by NAD(P)H to undergo conversion into formazan pigments. Specific examples of the tetrazolium salts include MTT (3-(4,5-dimethyl-2-thiazolyl)-2,5-diphenyl-2H-tetrazolium bromide), XTT (2,3-bis-(2-methoxy-4-nitro-5-sulfophenyl)-2H-tetrazolium-5-carboxanilide), MTS (3-(4,5-dimethylthiazol-2-yl)-5-(3-carboxymethoxyphenyl)-2-(4-sulfophenyl)-2H-tetrazolium), WST-1 (2-(4-iodophenyl)-3-(4-nitrophenyl)-5-(2,4-disulfophenyl)-2H-tetrazolium), and WST-8 (2-(2-methoxy-4-nitrophenyl)-3-(4-nitrophenyl)-5-(2,4-disulfophenyl)-2H-tetrazolium). Among these, WST-1 and WST-8 are preferred.

Since the absorption spectrum of the oxidation-reduction indicator varies depending on the indicator, the detection conditions for the color reaction may be appropriately set depending on the oxidation-reduction indicator employed.

In the method of the present invention, the concentration of the oxidation-reduction indicator is not limited as long as the color reaction proceeds depending on the cariogenic bacterial count in the test sample, and the concentration may be appropriately set depending on conditions such as the type of the oxidation-reduction indicator employed and other components. For example, in cases where the measurement of the cariogenic bacterial count is carried out using a test piece, the concentration of the oxidation-reduction indicator in the reagent impregnating solution used for preparation of the test piece is preferably 0.01 to 1 mM, more preferably 0.05 to 0.3 mM, still more preferably 0.1 to 0.16 mM.

In the present invention, the test reagent contains an oxidation-reduction promoter. In the present invention, the oxidation-reduction promoter is not limited as long as it is a compound that promotes a color reaction of an oxidation-reduction indicator by oxidation-reduction reaction. Examples of the oxidation-reduction promoter include compounds having a function to be reduced by NAD(P)H and thus converted into a reduced form, which can then reduce another substance. Examples of such another substance reduced by the reduced oxidation-reduction promoter include oxidation-reduction indicators. Specific examples of the oxidation-reduction promoter include 1-methoxy-5-methylphenazinium methyl sulfate (1-methoxy PMS), phenazinium methyl sulfate (PMS), and phenazine ethosulfate (PES). Among these, 1-methoxy PMS is preferred. Each of these may be contained alone, or an arbitrary combination of these may be contained.

In the method of the present invention, the concentration of the oxidation-reduction promoter is not limited as long as the color reaction proceeds depending on the cariogenic bacterial count in the test sample, and the concentration may be appropriately set depending on conditions such as the type of the oxidation-reduction promoter employed and other components. For example, the concentration of the oxidation-reduction promoter in the reagent impregnating solution is preferably 0.01 to 5 mM, more preferably 0.05 to 1 mM, still more preferably 0.1 to 0.6 mM.

In the present invention, the test reagent contains a halogen salt. In the present invention, the halogen salt refers to a salt in which a halogen ion is ionically bonded to an arbitrary cation. Examples of the halogen salt include fluoride salts, chloride salts, bromide salts, and iodide salts. The halogen salt is preferably a chloride salt or bromide salt, or more preferably a chloride salt. The halogen salt is preferably a salt of a halogen and an alkali metal. The alkali metal is preferably sodium or potassium. Preferred specific examples of the halogen salt include sodium chloride, potassium chloride, sodium bromide, and potassium bromide. Each of these may be contained alone, or an arbitrary combination of these may be contained.

In the method of the present invention, the concentration of the halogen salt is not limited as long as the color reaction proceeds depending on the cariogenic bacterial count in the test sample, and the concentration may be appropriately set depending on conditions such as the type of the halogen salt employed and other components. For example, the concentration of the halogen salt in the reagent impregnating solution is preferably 1 to 1000 mM, more preferably 5 to 500 mM, especially preferably 50 to 200 mM.

By inclusion of the halogen salt, for example, a decreased background in the color reaction can be expected. Specifically, for example, in cases where the oxidation-reduction indicator is resazurin and the oxidation-reduction promoter is 1-methoxy PMS, the blue color of resazurin is shifted toward the red-color side when resazurin and 1-methoxy PMS were used as a mixture thereof as compared to when resazurin alone is used, but addition of a halogen salt enables restoration of the color of resazurin to the blue-color side. Since, as described above, resazurin (blue) is reduced by NAD(P)H into resorufin (reddish purple), shifting of the blue color of resazurin toward the red-color side means an increase in the background of the color reaction, and also means that the possible range of color change is limited by the shift. Therefore, restoration of the color of resazurin to the blue-color side by the halogen salt means a decrease in the background of the color reaction, and also means that the possible range of color change can be expanded. Therefore, in the method of the present invention, the presence of a halogen salt enables clearer measurement of the color change as compared to cases where the halogen salt is absent. Thus, the halogen salt is effective for measurement of the cariogenic bacterial count based on the color change.

Further, as long as the color reaction proceeds depending on the cariogenic bacterial count in the test sample, the test reagent may contain another component.

The test reagent preferably contains, for example, a carbon source. The carbon source can preferably be metabolized by cariogenic bacteria so that metabolism in cariogenic bacteria can be activated. Examples of the carbon source include sugars and organic acids, and sugars are preferred. Specific examples of the sugars include sucrose and glucose, and sucrose is especially preferred. In cases where a carbon source is contained, the concentration of the carbon source in the reagent impregnating solution is preferably 1 to 1000 mM, more preferably 5 to 500 mM, especially preferably 20 to 250 mM.

The test reagent may also contain, for example, a pH buffering agent. Specific examples of the pH buffering agent include phosphate buffer, HEPES buffer, PIPES buffer, MES buffer, Tris buffer, and GTA wide range buffer. In cases where the pH buffering agent is contained, the concentration of the pH buffering agent in the reagent impregnating solution is preferably 10 to 1000 mM, more preferably 20 to 500 mM, especially preferably 50 to 150 mM. The pH of the reaction solution is, for example, usually pH 4.0 to 9.0, preferably 5.5 to 8.0.

The test reagent may also contain, for example a binder. Specific examples of the binder include polyvinyl alcohol (PVA), polyethylene glycol (PEG), polyvinyl pyrrolidone (PVP), and carboxymethyl cellulose. In cases where the binder is contained, the concentration of the binder in the reagent impregnating solution is preferably 0.01 to 5%, more preferably 0.05 to 3%, still more preferably 0.1 to 1%. In the present invention, "%" for the binder concentration means w/v % unless otherwise specified.

The test reagent may also contain, for example, an agent that inhibits metabolism in bacteria other than cariogenic bacteria. Specific examples of such an agent include agents to be used for growth inhibition of bacteria other than cariogenic bacteria, such as bacitracin, and agents that suppress the growth of Gram-negative bacteria, such as potassium tellurite.

Each of these components may be contained alone, or an arbitrary combination of these components may be contained.

The method of the present invention can be carried out using a test piece. The test piece used for the method of the present invention (hereinafter also referred to as the test piece of the present invention) is a test piece holding a test reagent containing an oxidation-reduction indicator, oxidation-reduction promoter, and halogen salt. The test piece of the present invention may be a test piece for measuring NAD(P)H, and an embodiment thereof is a test piece for use in measurement of the cariogenic bacterial count. The test piece of the present invention is described below by way of example of the test piece to be used for measurement of the cariogenic bacterial count.

The test piece of the present invention preferably comprises a support carrier and an absorption carrier carried by the support carrier, which absorption carrier holds the test reagent. By spotting a test sample on the absorption carrier portion holding the test reagent, a color reaction proceeds depending on the cariogenic bacterial count in the test sample. FIG. 1 shows an example of a test piece 1 as an embodiment of the test piece of the present invention, which test piece 1 comprises a support carrier 10 and an absorption carrier 11 carried by the support carrier 10. FIG. 1(A) is a plan view of the test piece 1, and FIG. 1(B) is a front view of the test piece 1.

As the absorption carrier, any carrier may be used as long as it can hold the test reagent and enables measurement of the color change due to reduction of the oxidation-reduction indicator. That is, examples of the absorption carrier include paper, cellulose, porous ceramics, chemical fibers, synthetic resin-woven fabrics, and non-woven fabrics. The absorption carrier is preferably filter paper or glass fiber filter paper. For example, a commercially available filter paper or glass fiber filter paper may be preferably used.

Preferred examples of the support carrier include flat carriers such as films, sheets, and plates. The support carrier may be made of plastic or paper. Examples of the plastic include various plastics such as polyethylene, polypropylene, polyester, and polyvinyl chloride. For example, the support carrier is preferably a polyethylene terephthalate (PET) carrier. The support carrier may be a composite material, and composite materials of polyester and polyethylene, composite materials prepared by laminating polyethylene and aluminum, and other various composite materials may be used. The thickness of the support carrier is preferably 10 to 500 μm, more preferably 50 to 300 μm.

The test piece of the present invention may comprise at least one absorption carrier holding the test reagent for measuring the cariogenic bacterial count, or may comprise 2 or more such carriers.

The test piece of the present invention may further comprise, in addition to the absorption carrier holding the test reagent for measuring the cariogenic bacterial count, an absorption carrier for measurement of a parameter other than the cariogenic bacterial count. Further, in addition to the absorption carrier(s) for measurement of a parameter(s) such as the cariogenic bacterial count, the test piece of the present invention may comprise an arbitrary test paper, for example, a dummy absorption carrier that is not used for measurement of any parameter. In cases where the test piece of the present invention comprises a plurality of absorption carriers, each absorption carrier may be arranged appropriately depending on the type of the detector used or the like. As the detector, various reflectometers may preferably be used, and, in cases where PocketChem UA PU-4010 (manufactured by Arkray, Inc.) is used as the detector, each absorption carrier is preferably arranged linearly on the support carrier.

The method for producing the test piece of the present invention is not limited. The test piece of the present invention can be produced by, for example, preliminarily making an absorption carrier hold a test reagent, and then making a support carrier carry the resulting absorption carrier. The method to make the absorption carrier hold the reagent is not limited, and, for example, the absorption carrier may be soaked in a reagent solution, or a reagent solution may be spotted on or applied to the absorption carrier. Among these, soaking of the absorption carrier in a reagent solution is preferred. The reagent solution refers to a solution containing a test reagent. The process of making an absorption carrier hold a reagent may comprise a plurality of steps of soaking, spotting, or application. The absorption carrier holding a reagent may be dried and then used in the later steps. By cutting, as required, the absorption carrier holding a reagent and making a support carrier carry the absorption carrier, the test piece of the present invention can be produced. The test piece of the present invention may also be produced, for example, by preliminarily making a support carrier carry an absorption carrier and then making the absorption carrier hold a test reagent. In such a case, it is preferred that the reagent solution is spotted on or applied to the absorption carrier, thereby making the absorption carrier hold the reagent, followed by drying the carrier. In the test piece of the present invention, the method for making the support carrier carry the absorption carrier is not limited, and, for example, an adhesion method that is normally used may be preferably used. For example, the adhesion may be carried out by using a sticky tape or an adhesive agent.

By the method of the present invention, the cariogenic bacterial count can be measured without controlling the temperature. That is, the reaction temperature may be room temperature. More specifically, the reaction temperature is usually 15° C. to 37° C., or may be 15° C. to 30° C. In the method of the present invention, the temperature may also be controlled as appropriate.

In the method of the present invention, the reaction time may be appropriately set depending on conditions such as the reaction temperature and the reagent component. The reaction time is, for example, usually 1 to 10 minutes. For example, the reaction time may also be 5 minutes.

In the method of the present invention, the cariogenic bacterial count can be measured based on the measured color change. "Measurement of the cariogenic bacterial count" is not limited to calculation of the value itself of the cariogenic bacterial count in the test sample, but may also refer to judgment of the degree of the cariogenic bacterial count in the test sample by rating at least on a 2-point scale, preferably on a 3 or more point scale. Specifically, for example, the cariogenic bacterial count in the test sample may be judged as any of the 3 ranks: "low", "medium", and "high". The specific bacterial counts for rating into a plurality of ranks may be appropriately set depending on clinical data and the mode of the test sample used. For example, in terms of the cariogenic bacterial count in a mouth wash solution obtained after rinsing the mouth for 10 seconds with 3 mL of purified water, the bacterial count may be judged as "low" when the count is lower than $10^6$ CFU/mL, "medium" when the count is $10^6$ CFU/mL or more and lower than $10^7$ CFU/mL, and "high" when the count is $10^7$ CFU/mL or more.

The color change, the value of the cariogenic bacterial count, or the degree of the cariogenic bacterial count measured by the method of the present invention may be used for judging the caries risk in the subject from whom the test sample was collected. For example, based on the color change, the value of the cariogenic bacterial count, or the degree of the cariogenic bacterial count, the caries risk in the subject from whom the test sample was collected may be judged by rating at least on a 2-point scale, preferably on a 3 or more point scale. Specifically, the caries risk in the subject from whom the test sample was collected may be judged as any of the 3 ranks: "low", "medium", and "high". In the method of the present invention, such judgment of the caries risk is also included in the "measurement of the cariogenic bacterial count". The color change, the value of the cariogenic bacterial count, or the degree of the cariogenic bacterial count measured by the method of the present invention may be used alone for judgment of the caries risk, or may be used in combination with other parameter(s).

The measurement of the cariogenic bacterial count based on the color change may be carried out by obtaining correlation data between the cariogenic bacterial count and the color change using standard samples of cariogenic bacteria having known bacterial counts, and utilizing the obtained correlation data. For example, the correlation data is a calibration curve. Further, judgment of the caries risk may be carried out by utilizing correlation data including the caries risk.

In the method of the present invention, the color change refers to an increase or decrease in the absorbance at a specific wavelength and/or a shift of the maximum absorption wavelength caused by reduction of the oxidation-reduction indicator. That is, in the method of the present invention, partial or total reduction of the oxidation-reduction indicator causes an increase or decrease in the absorbance at a specific wavelength and/or a shift of the maximum absorption wavelength depending on the amount and/or ratio of the reduced oxidation-reduction indicator.

In the method of the present invention, the color change can be measured with an optical detector. The color change is preferably measured as an increase or decrease in the absorbance at a specific wavelength.

The increase or decrease in the absorbance at a specific wavelength can be usually measured by irradiating the coloration site, i.e. the absorption carrier portion on which the test sample was spotted, with light having the specific wavelength and obtaining the value of change in the reflectance at the specific wavelength during a predetermined period of time. An increase in the absorbance at a specific wavelength can be measured as a decrease in the reflectance at the specific wavelength. A decrease in the absorbance at a specific wavelength can be measured as an increase in the reflectance at the specific wavelength. The predetermined period of time may be a period from immediately after spotting of the test sample to an arbitrary time point thereafter, or may be a period from a certain time point after spotting of the test sample to an arbitrary time point thereafter. The length of the predetermined period of time may be appropriately set depending on conditions such as the reaction time, and, for example, the length is usually 1 to 10 minutes, or may be 2 to 8 minutes. The certain time point after spotting of the test sample may be appropriately set depending on conditions such as the reaction time, and, for example, the certain time point is preferably 5 seconds to 3 minutes after spotting of the test sample, more preferably 10 seconds to 2 minutes after spotting of the test sample. Specifically, when the reaction time is 5 minutes, the change in the reflectance may be measured for 4 minutes between Minute 1 and Minute 5 after the start of the reaction. The value of change in the reflectance can be calculated as the difference between measured values of the reflectance obtained by measuring the reflectance at least twice. The reflectance may also be measured 3 or more times. The value of change in the reflectance during a predetermined period of time may also be calculated as the rate of change in the reflectance based on reflectance values obtained by measuring the reflectance a plurality of times.

In cases where there is no need to measure the reflectance immediately after the spotting of the test sample or at a certain time point after the spotting of the test sample, the number of times of measurement of the reflectance can be reduced. For example, if the reflectance value immediately after the spotting of the test sample or at a certain time point after the spotting of the test sample is regarded as constant independently of the cariogenic bacterial count in the test sample, it is also possible to measure the reflectance only once at an arbitrary period of time thereafter and calculate the value of change in the reflectance as the difference between the measured value and the constant value. The constant value may be determined before or upon calculation of the value of change in the reflectance. In cases where the reflectance value immediately after the spotting of the test sample or at a certain time point after the spotting of the test sample is regarded as constant independently of the cariogenic bacterial count in the test sample, correlation data between the reflectance and the cariogenic bacterial count at an arbitrary time point thereafter may be utilized to measure the cariogenic bacterial count without calculating the value of change in the reflectance itself. In such cases where the cariogenic bacterial count is measured without calculating the value of change in the reflectance itself, the measurement of the reflectance itself may be regarded as "measurement of an increase or decrease in the absorbance", and may also be regarded as "measurement of the color change" in the method of the present invention. That is, such cases where the cariogenic bacterial count is measured without calculating the value of change in the reflectance itself are also included in the measurement of the cariogenic bacterial count based on the color change.

The increase or decrease in the absorbance may be measured based on at least one measurement wavelength, or may be measured based on 2 or more wavelengths including at least one measurement wavelength. For example, 2 or more measurement wavelengths may be used, or a measurement length and a reference wavelength for removal of the background may be individually set and used. The wavelength of the light source for measuring the increase or decrease in the absorbance may be appropriately set depending on the oxidation-reduction indicator and the detector used. The measurement wavelength may be the maximum absorption wavelength of either the oxidized form or reduced form of the oxidation-reduction indicator used, or may be another wavelength. For example, in cases where resazurin is used as the oxidation-reduction indicator, the measurement wavelength may be 630 to 635 nm, and the reference wavelength may be 750 to 760 nm.

The shift of the maximum absorption wavelength can be measured by comparing the maximum absorption wavelengths observed before and after the elapse of a certain period of time. The maximum absorption wavelength can be identified by irradiating the coloration site, i.e. the absorption carrier portion on which the test sample was spotted, with light having a plurality of wavelengths and measuring the reflectance at each wavelength. The conditions for measuring the shift of the maximum absorption wavelength may be the same as those for measuring the increase or decrease in the absorbance at a specific wavelength, except that light having a plurality of wavelengths is used to specify the maximum absorption wavelength.

The data as described above obtained for measuring the color change, that is, the reflectance(s) at a specific wavelength(s), the value of change in the reflectance calculated therefrom, the maximum absorption wavelength, and the like, may be hereinafter collectively referred to as the "reflectance data".

The optical detector is not limited, and examples of the optical detector that may be used include reflectometers for urine test paper or blood test paper. For example, as a reflectometer for urine test paper, PocketChem UA PU-4010 (manufactured by Arkray, Inc.) may be used. In cases where PocketChem UA PU-4010 is used, measurement by two-wavelength reflectance photometry may be carried out. In PocketChem UA PU-4010, the photometer section radiates, from multi-LED, 2 kinds of light having different wavelengths, i.e. light having a measurement wavelength and light having a reference wavelength, to the coloration site. Based on their reflectances, the color change can be measured.

Specifically, in cases where a test piece using resazurin is used as the oxidation-reduction indicator and PocketChem UA PU-4010 (manufactured by Arkray, Inc.) is used as the detector, the measurement can be carried out at room temperature with a reaction time of 5 minutes, at a measurement wavelength of 635 nm and a reference wavelength of 760 nm. Under these conditions, the progress of reduction reaction of resazurin is detected as a decrease in the absorbance at 635 nm, that is, as an increase in the reflectance upon radiation of light at 635 nm. In cases where the reaction time is 5 minutes, for example, the change in the reflectance during the 4 minutes between Minute 1 and Minute 5 after the beginning of the reaction may be measured.

The method of the present invention may further comprise a step of outputting the measured color change, calculated value of the cariogenic bacterial count, judged degree of the cariogenic bacterial count, and/or judged degree of the caries risk, and may further comprise a step of outputting a comment based on these measurement or judgment results. The comment is, for example, one explaining the measurement or judgment results. Examples of the comment include "The saliva contains only a small amount of cariogenic bacteria. The condition is good." The output can be carried out by, for example, displaying on a display portion provided in the reflectometer. The display portion is not limited as long as it can show information such as letters and images, and preferred examples of the display portion include liquid crystal displays provided with an LED backlight. The display is carried out in an arbitrary form such as letters, figures, symbols, or colors, or a combination thereof. The mode of output is not limited as long as the output information can be recognized by a doctor, dental hygienist, subject, or the like, and, for example, the output may be carried out by printing or sound. The output of information may also be carried out by an arbitrary combination of visual display on the display portion, output by printing, output by sound, and the like.

In the method of the present invention, the respective steps, i.e. obtaining reflectance data, operations such as calculation of the cariogenic bacterial count, output of the measurement or judgment results and the comment, and the like, may be carried out by either a single computer or a plurality of physically independent computers. For example, the obtained reflectance data may be sent to another device using an electric communication line or the like, and the operations such as calculation of the cariogenic bacterial count may be carried out by the other device. Also, the measurement or judgment results may be sent to another device using an electric communication line or the like, and information such as the measurement or judgment results, comments based thereon, and the like may be displayed in the other device. Examples of such a mode include a mode in which the reflectance data is input on the WEB and sent to an operation server, operations such as calculation of the cariogenic bacterial count are carried out in the operation server, and then the measurement or judgment results are displayed on the WEB. Further, a charging system based on transmission and reception of data using an electric communication line or the like may be employed. Examples of such a charging system include a system in which charging occurs when the measurement or judgment results are displayed by the user in a WEB browser or when the user completed downloading a file containing the measurement or judgment results. The charging may be carried out by an arbitrary method such as a display or download-based metered-rate system, or a flat-rate system in which the charging occurs dependently on the length of period of time such as days, weeks, or months.

Although the method of the present invention was described above by way of example of the method for measuring the cariogenic bacterial count, use of the method of the present invention is not limited to measurement of the cariogenic bacterial count, and the method can be applied to an arbitrary method utilizing detection of NAD(P)H contained in a test sample and/or NAD(P)H produced in a reaction system. For example, the method of the present invention can be used for detection of an enzyme reaction by which NAD(P)H is directly or indirectly produced. The object of the method of the present invention may or may not be measurement of NAD(P)H itself. The above description about the method for measuring the cariogenic bacterial count, and about the test reagent, test piece, and the like related thereto may also be applied mutatis mutandis to other modes of the method of the present invention. For example, the method of the present invention may comprise, depending its mode, a step of calculating the amount or degree of NAD(P)H based on the measured color change, or a step of calculating the amount or degree of a subject to be detected that is related to the amount of NAD(P)H, based on the measured color change.

Further, depending on conditions such as the object of measurement, the method of the present invention is not limited to modes in which a test piece is used as described above, and the color reaction may proceed in any other arbitrary mode. For example, in the method of the present invention, the color reaction may proceed in a container containing the above test reagent. Specifically, by placing the test sample and the test reagent in a arbitrary container, the color reaction can proceed depending on the amount of NAD(P)H contained in the test sample and/or the amount of NAD(P)H produced in the container. The container is not limited, and examples of the container include tubes and test tubes.

Further, depending on conditions such as the object of measurement, the method of the present invention is not limited to modes in which a detector is used as described above, and the color reaction may be detected in any other arbitrary mode. For example, in the method of the present invention, the color change may be measured by the naked eye. However, in order to utilize the effect of the halogen salt to reduce the background of the color reaction effectively, it is preferred to use an optical detector to measure the color change quantitatively, and it is also preferred to perform quantitative measurement of the cariogenic bacterial count or the like based on a quantitative measurement result on the color change.

Further, in the method of the present invention, depending on conditions such as the object of measurement, as long as the oxidation-reduction indicator, oxidation-reduction promoter, and halogen salt are used as the effective components, the reaction system may or may not contain the test sample and all of these effective components from the beginning of the reaction. For example, addition of the test reagent to the reaction system may be carried out after sufficient progress of production of NAD(P)H in the test sample. Further, for example, the effective components each may be added to the reaction system at different timings. For obtaining the effect of the halogen salt to reduce the background of the color reaction, usually, the halogen salt is preferably added before completing addition of all of the test sample, oxidation-reduction indicator, and oxidation-reduction promoter to the reaction system, and the halogen salt is more preferably preliminarily added to the oxidation-reduction indicator or a mixture of the oxidation-reduction indicator and the oxidation-reduction promoter.

Further, in the present invention, the test reagent may be provided in an arbitrary mode as long as the test reagent contains the effective components. For example, the test reagent may be provided in a form of being held in the test piece as described above, or may be provided in a form of being contained in an arbitrary container. Further, the test reagent may be provided after formulation into an arbitrary form such as a solid, liquid, or gel. For the formulation, additives such as vehicles, binders, disintegrators, lubricants, stabilizers, correctives, diluents, surfactants, and solvents that are usually used as formulation carriers may be used. The test reagent may be used in the method of the present invention as it is, or after being diluted, dispersed, or dissolved in water, physiological saline, buffer, or the like. Needless to say, the test reagent is included within the scope of the present invention even in cases where such dilution, dispersion, or dissolution is carried out. The effective components may be contained in the test reagent in a form of being mixed with each other, or may be individually contained in the respective test reagents without mixed with each other. The concentration of each effective component in the test reagent of the present invention may be appropriately set in consideration of conditions such as the object of measurement, and, for example, the concentration may be such a concentration that the concentration in a liquid state in which the effective component is mixed with the test sample in the reaction system is a preferred concentration in the above-described reagent impregnating solution.

Further, the test reagent of the present invention may be provided as a kit for, for example, measurement of NAD (P)H or measurement of the cariogenic bacterial count. The kit is not limited as long as it comprises the test reagent of the present invention.

EXAMPLES

The present invention is described more specifically below by way of Examples. However, the present invention is not limited to these Examples.

Experiment Example 1

Determination of Sensitizer

In the present Experiment Example, screening was carried out for compounds that can be used as a sensitizer when resazurin is used as the oxidation-reduction indicator.

<Formulation of Reagent Impregnating Solution>

In 1100 mL of distilled water, 42 mg of sodium resazurin (manufactured by Tokyo Chemical Industry Co., Ltd.), 120 mL of 1 M phosphate buffer (pH 6.0), and 12 g of sucrose (manufactured by Nacalai Tesque) were dissolved to prepare a basic composition, and test components each were added to the prepared basic composition to give the concentrations shown in Table 1, and thus to prepare reagent impregnating solutions.

TABLE 1

| | Formulation of reagent impregnating solution | | | | | | | | |
|---|---|---|---|---|---|---|---|---|---|
| | | Buffer | | Carbon | Test component | | | | |
| | Pigment Resazurin | Phosphate buffer pH6.0 | Binder PVA | source Sucrose | 1-Methoxy PMS | Diaphorase | Lysozyme | Urea | TritonX100 |
| Comparative Example 1 | Manufactured by Tokyo Chemical Industry Co., Ltd. | Manufactured by Nacalai Tesque | Manufactured by Kuraray Co., Ltd. | Manufactured by Nacalai Tesque | Manufactured by Dojindo Laboratories | Manufactured by Unitika Ltd. | Manufactured by SIGMA | Manufactured by Nacalai Tesque | Manufactured by Wako Pure Chemical Industries, Ltd. |
| Comparative Example 2 | 0.12 mM | 0.1M | 0.2% | 30 mM | 0.5 mM | — | — | — | — |
| Comparative Example 3 | 0.12 mM | 0.1M | 0.2% | 30 mM | — | — | — | — | — |
| Comparative Example 4 | 0.12 mM | 0.1M | 0.2% | 30 mM | — | 3 U/mL | — | — | — |
| Comparative Example 5 | 0.12 mM | 0.1M | 0.2% | 30 mM | — | 10 U/mL | — | — | — |
| Comparative Example 6 | 0.12 mM | 0.1M | 0.2% | 30 mM | — | — | — | 0.1M | — |
| Comparative Example 7 | 0.12 mM | 0.1M | 0.2% | 30 mM | — | — | — | 0.5M | — |

TABLE 1-continued

Formulation of reagent impregnating solution

| | Buffer | | | Carbon | Test component | | | | |
| | Pigment Resazurin | Phosphate buffer pH6.0 | Binder PVA | source Sucrose | 1-Methoxy PMS | Diaphorase | Lysozyme | Urea | TritonX100 |
|---|---|---|---|---|---|---|---|---|---|
| Comparative Example 8 | 0.12 mM | 0.1M | 0.2% | 30 mM | — | — | 1 mg/mL | — | — |
| Comparative Example 9 | 0.12 mM | 0.1M | 0.2% | 30 mM | — | — | 3 mg/mL | — | — |
| Comparative Example 10 | 0.12 mM | 0.1M | 0.2% | 30 mM | — | — | 10 mg/mL | — | — |
| Comparative Example 11 | 0.12 mM | 0.1M | 0.2% | 30 mM | — | — | — | — | 0.01% |
| Comparative Example 12 | 0.12 mM | 0.1M | 0.2% | 30 mM | — | — | — | — | 0.10% |
| Comparative Example 13 | 0.12 mM | 0.1M | 0.2% | 30 mM | — | — | — | — | 1.00% |

<Preparation of Test Pieces>

After impregnating filter paper with each of the reagent impregnating solutions described above, the resulting filter paper was dried at 50° C. for 15 minutes, to obtain test paper. The prepared test paper was cut into a piece of 5 mm×300 mm, and the resulting piece was attached to a PET film of 100 mm×280 mm on which an adhesive agent was attached. The resulting PET film having the test piece attached thereon was cut into a width of 5 mm, to obtain a test piece of 100 mm×5 mm. The test paper portion on which the reagent is held may be hereinafter referred to as the "reagent portion".

<Measurement Method>

On the reagent portion of the test piece, 10 μL of a bacterial suspension of Streptococcus mutans (ATCC25175) prepared by suspending the bacteria in distilled water such that the density was $10^9$ CFU/mL was dropped, and the resultant was left to stand at room temperature. The change in the reflectance between Minute 1 and Minute 5 at a measurement wavelength of 635 nm and reference wavelength of 760 nm (also referred to as the Δ 4-minute reflectance) was measured for each test paper using a reflectometer.

<Results>

Figure 2:
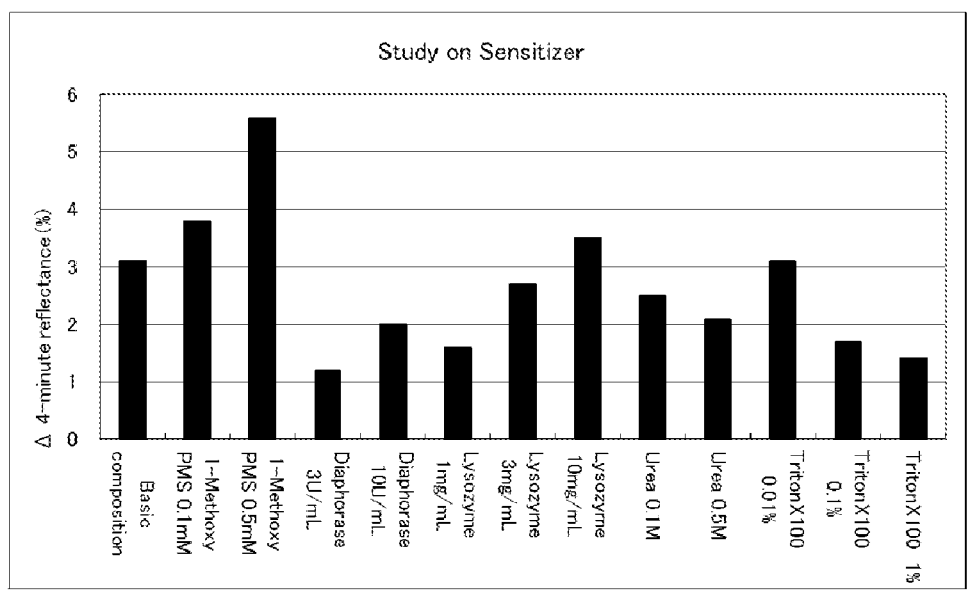
FIG. 2 is a diagram illustrating the effect of each test component on the change in the reflectance observed during the period between Minute 1 and Minute 5 after the beginning of the reaction (Δ 4-minute reflectance).

The results are shown in FIG. 2. As a result of the study, it was found that addition of 1-methoxy PMS to the basic composition remarkably increases the Δ 4-minute reflectance.

Experiment Example 2

Determination of Base Reflectance Reducing Agent

In the present Experiment Example, screening was carried out for compounds that can reduce the base reflectance (i.e. the background value of the reflectance) when resazurin is used as the oxidation-reduction indicator and 1-methoxy PMS is used as the sensitizer.

<Formulation>

In 1100 mL of distilled water, 42 mg of sodium resazurin (manufactured by Tokyo Chemical Industry Co., Ltd.), 120 mL of 1 M phosphate buffer (pH 6.0), 12 g of sucrose (manufactured by Nacalai Tesque), and 242 mg of 1-methoxy PMS (manufactured by Dojindo Laboratories) were dissolved to prepare a basic composition, and test components each were added to the prepared basic composition to give the concentrations shown in Table 2, and thus to prepare reagent impregnating solutions.

TABLE 2

Formulation of reagent impregnating solution

| | Pigment Resazurin Manufactured by Tokyo Chemical Industry Co., Ltd. | Buffer Phosphate buffer pH60 Manufactured by Nacalai Tesque | Binder PVA Manufactured by Kuraray Co., Ltd. | Carbon source Sucrose Manufactured by Nacalai Tesque | Sensitizer 1-Methoxy PMS Manufactured by Dojindo Laboratories | Test component | | | | | | | | |
| | | | | | | NaCl Manufactured by Nacalai Tesque | KCl Manufactured by Nacalai Tesque | NAD Manufactured by Oriental Yeast Co., Ltd. | $KH_2PO_4$ Manufactured by Nacalai Tesque | $Na_2HPO_4$ Manufactured by Nacalai Tesque | ADP Manufactured by Oriental Yeast Co., Ltd. | Trisodium citrate Manufactured by Wako Pure Chemical Industries, Ltd. | Trisodium isocitrate Manufactured by SIGMA | Potassium pyruvate Manufactured by Nacalai Tesque | Sodium glutamate Manufactured by Nacalai Tesque |
|---|---|---|---|---|---|---|---|---|---|---|---|---|---|---|---|
| Comparative Example 14 | 0.14 mM | 0.1M | 0.0% | 30 mM | 0.4 mM | — | — | — | — | — | — | — | — | — | — |

TABLE 2-continued

Formulation of reagent impregnating solution

| | Pigment Resazurin (Tokyo Chemical Industry Co., Ltd.) | Buffer Phosphate buffer pH6.0 (Nacalai Tesque) | Binder PVA (Kuraray Co., Ltd.) | Carbon source Sucrose (Nacalai Tesque) | Sensitizer 1-Methoxy PMS (Dojindo Laboratories) | Test component | | | | | | | | | |
|---|---|---|---|---|---|---|---|---|---|---|---|---|---|---|---|
| | | | | | | NaCl (Nacalai Tesque) | KCl (Nacalai Tesque) | NAD (Oriental Yeast Co., Ltd.) | $KH_2PO_4$ (Nacalai Tesque) | $Na_2HPO_4$ (Nacalai Tesque) | ADP (Oriental Yeast Co., Ltd.) | Trisodium citrate (Wako Pure Chemical Industries, Ltd.) | Trisodium isocitrate (SIGMA) | Potassium pyruvate (Nacalai Tesque) | Sodium glutamate (Nacalai Tesque) |
| Example 1 | 0.14 mM | 0.1M | 0.0% | 30 mM | 0.4 mM | 50 mM | — | — | — | — | — | — | — | — | — |
| Example 2 | 0.14 mM | 0.1M | 0.0% | 30 mM | 0.4 mM | 150 mM | — | — | — | — | — | — | — | — | — |
| Example 3 | 0.14 mM | 0.1M | 0.0% | 30 mM | 0.4 mM | 200 mM | — | — | — | — | — | — | — | — | — |
| Example 4 | 0.14 mM | 0.1M | 0.0% | 30 mM | 0.4 mM | — | 50 mM | — | — | — | — | — | — | — | — |
| Example 5 | 0.14 mM | 0.1M | 0.0% | 30 mM | 0.4 mM | — | 150 mM | — | — | — | — | — | — | — | — |
| Example 6 | 0.14 mM | 0.1M | 0.0% | 30 mM | 0.4 mM | — | 200 mM | — | — | — | — | — | — | — | — |
| Comparative Example 15 | 0.14 mM | 0.1M | 0.0% | 30 mM | 0.4 mM | — | — | 0.6 mM | — | — | — | — | — | — | — |
| Comparative Example 16 | 0.14 mM | 0.1M | 0.0% | 30 mM | 0.4 mM | — | — | 6 mM | — | — | — | — | — | — | — |
| Comparative Example 17 | 0.14 mM | 0.1M | 0.0% | 30 mM | 0.4 mM | — | — | — | 1.1 mM | 3 mM | — | — | — | — | — |
| Comparative Example 18 | 0.14 mM | 0.1M | 0.0% | 30 mM | 0.4 mM | — | — | — | 0.4 mM | 1 mM | — | — | — | — | — |
| Comparative Example 19 | 0.14 mM | 0.1M | 0.0% | 30 mM | 0.4 mM | — | — | — | — | — | 0.5 mM | — | — | — | — |
| Comparative Example 20 | 0.14 mM | 0.1M | 0.0% | 30 mM | 0.4 mM | — | — | — | — | — | 5 mM | — | — | — | — |
| Comparative Example 21 | 0.14 mM | 0.1M | 0.0% | 30 mM | 0.4 mM | — | — | — | — | — | — | 30 mM | — | — | — |
| Comparative Example 22 | 0.14 mM | 0.1M | 0.0% | 30 mM | 0.4 mM | — | — | — | — | — | — | 60 mM | — | — | — |
| Comparative Example 23 | 0.14 mM | 0.1M | 0.0% | 30 mM | 0.4 mM | — | — | — | — | — | — | — | 30 mM | — | — |
| Comparative Example 24 | 0.14 mM | 0.1M | 0.0% | 30 mM | 0.4 mM | — | — | — | — | — | — | — | 60 mM | — | — |
| Comparative Example 25 | 0.14 mM | 0.1M | 0.0% | 30 mM | 0.4 mM | — | — | — | — | — | — | — | — | 30 mM | — |

TABLE 2-continued

Formulation of reagent impregnating solution

| | Pigment Resazurin Manufactured by Tokyo Chemical Industry Co., Ltd. | Buffer Phosphate buffer pH60 Manufactured by Nacalai Tesque | Binder PVA Manufactured by Kuraray Co., Ltd. | Carbon source Sucrose Manufactured by Nacalai Tesque | Sensitizer 1-Methoxy PMS Manufactured by Dojindo Laboratories | Test component | | | | | | | | | |
|---|---|---|---|---|---|---|---|---|---|---|---|---|---|---|---|
| | | | | | | NaCl Manufactured by Nacalai Tesque | KCl Manufactured by Nacalai Tesque | NAD Manufactured by Oriental Yeast Co., Ltd. | $KH_2PO_4$ Manufactured by Nacalai Tesque | $Na_2HPO_4$ Manufactured by Nacalai Tesque | ADP Manufactured by Oriental Yeast Co., Ltd. | Tri-sodium citrate Manufactured by Wako Pure Chemical Industries, Ltd. | Tri-sodium isocitrate Manufactured by SIGMA | Potassium pyruvate Manufactured by Nacalai Tesque | Sodium glutamate Manufactured by Nacalai Tesque |
| Comparative Example 26 | 0.14 mM | 0.1M | 0.0% | 30 mM | 0.4 mM | — | — | — | — | — | — | — | — | 60 mM | — |
| Comparative Example 27 | 0.14 mM | 0.1M | 0.0% | 30 mM | 0.4 mM | — | — | — | — | — | — | — | — | — | 30 mM |
| Comparative Example 28 | 0.14 mM | 0.1M | 0.0% | 30 mM | 0.4 mM | — | — | — | — | — | — | — | — | — | 60 mM |

<Preparation of Test Pieces>

After impregnating filter paper with each of the reagent impregnating solutions described above, the resulting filter paper was dried at 50° C. for 15 minutes, to obtain test paper. The prepared test paper was cut into a piece of 5 mm×300 mm, and the resulting piece was attached to a PET film of 100 mm×280 mm on which an adhesive agent was attached. The resulting PET film having the test piece attached thereon was cut into a width of 5 mm, to obtain a test piece of 100 mm×5 mm.

<Measurement Method>

First, the base reflectance of each test piece was measured. On the reagent portion of the test piece, 10 μL of distilled water was dropped, and the resultant was left to stand at room temperature. The reflectance at Minute 1 at a measure wavelength of 635 nm and reference wavelength of 760 nm was measured for each test paper using a reflectometer, to determine the base reflectance.

Further, the reactivity of each test piece to cariogenic bacteria was separately evaluated. On the reagent portion of the test piece, 10 μL of a bacterial suspension of *Streptococcus mutans* (ATCC25175) prepared by suspending the bacteria in distilled water such that the density was $10^9$ CFU/mL was dropped, and the resultant was left to stand at room temperature. The change in the reflectance between Minute 1 and Minute 5 at a measurement wavelength of 635 nm and reference wavelength of 760 nm (Δ 4-minute reflectance) was measured for each test paper using a reflectometer.

<Results>

Figure 3:
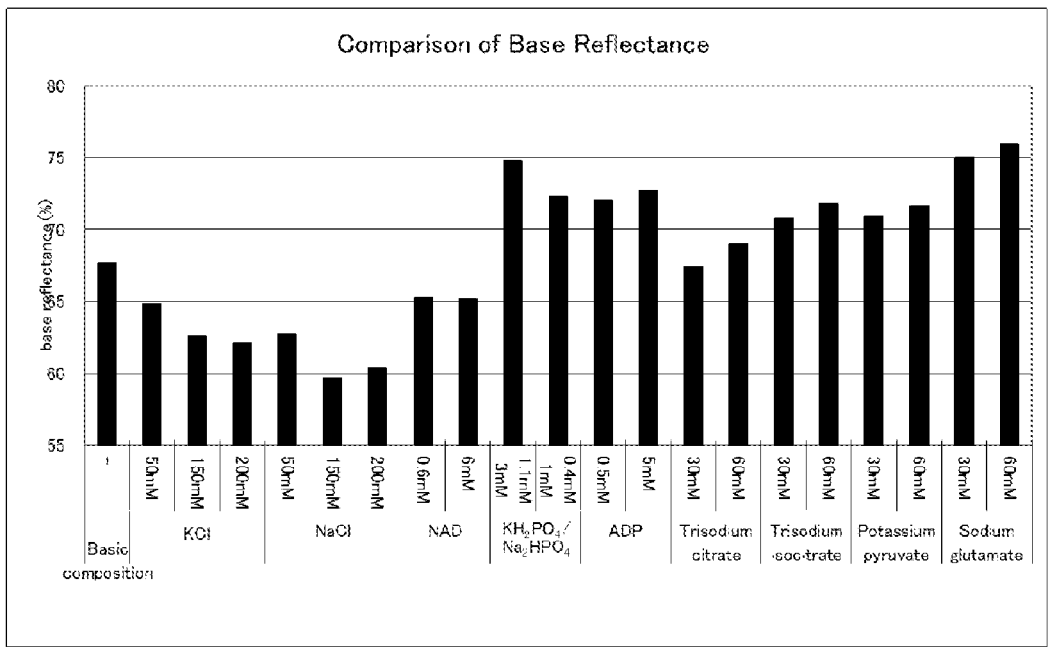
FIG. 3 is a diagram illustrating the effect of each test component on the base reflectance.

The results of measurement of the base reflectance are shown in FIG. 3. As a result of the study, it was found that addition of KCl or NaCl to the basic composition remarkably reduces the base reflectance.

Figure 4:
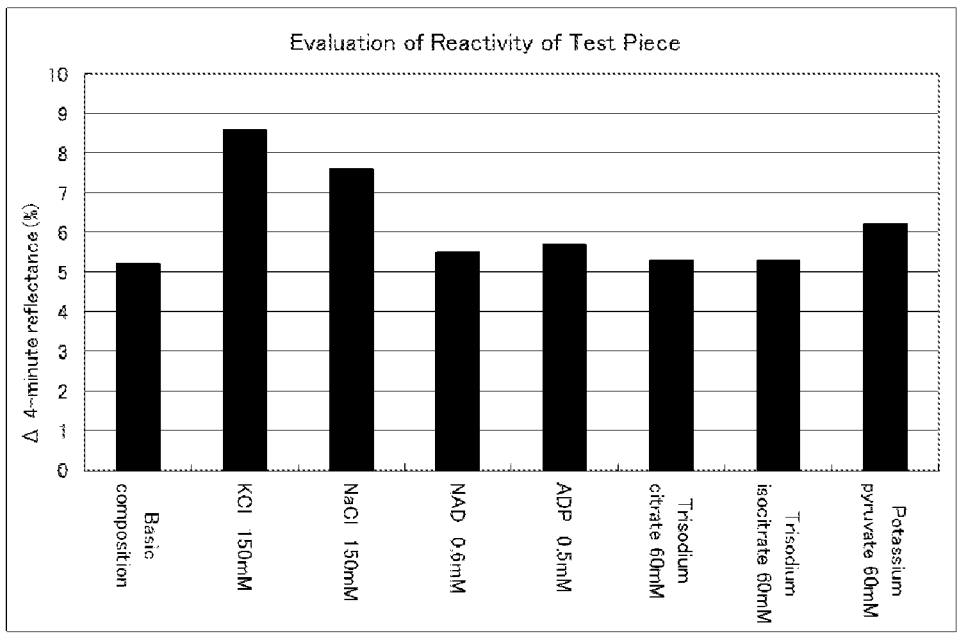
FIG. 4 is a diagram illustrating the effect of each test component on the Δ 4-minute reflectance.

Further, the results of evaluation of the reactivity are shown in FIG. 4. It was found that, as compared to the case where only the sensitizer 1-methoxy PMS was added, combined use with KCl or NaCl further increases the Δ 4-minute reflectance and remarkably improves the reactivity.

Experiment Example 3

Study Using Mouth Wash Solution

In the present Experiment Example, the effect of addition of KCl or NaCl was studied using a mouth wash solution as a test sample.

<Formulation>

In 1100 mL of distilled water, 42 mg of sodium resazurin (manufactured by Tokyo Chemical Industry Co., Ltd.), 120 mL of 1 M phosphate buffer (pH 6.0), and 12 g of sucrose (manufactured by Nacalai Tesque) were dissolved to prepare a basic composition, and 1-methoxy PMS and KCl or NaCl were added to the prepared basic composition to give the concentrations shown in Table 3, and thus to prepare reagent impregnating solutions.

TABLE 3

| | Pigment Resazurin Manufactured by Tokyo Chemical Industry Co., Ltd. | Buffer Phosphate buffer pH6.0 Manufactured by Nacalai Tesque | Binder PVA Manufactured by Kuraray Co., Ltd. | Carbon source Sucrose Manufactured by Nacalai Tesque | Sensitizer 1-Methoxy PMS Manufactured by Dojindo Laboratories | Salts | |
|---|---|---|---|---|---|---|---|
| | | | | | | KCl Manufactured by Nacalai Tesque | NaCl Manufactured by Nacalai Tesque |
| Comparative Example 29 | 0.14 mM | 0.1M | 0.0% | 30 mM | 0.4 mM | — | — |
| Comparative Example 30 | 0.14 mM | 0.1M | 0.0% | 30 mM | 0.5 mM | — | — |
| Comparative Example 31 | 0.14 mM | 0.1M | 0.0% | 30 mM | 0.6 mM | — | — |
| Example 7 | 0.14 mM | 0.1M | 0.0% | 30 mM | 0.4 mM | 150 mM | — |
| Example 8 | 0.14 mM | 0.1M | 0.0% | 30 mM | 0.5 mM | 150 mM | — |
| Example 9 | 0.14 mM | 0.1M | 0.0% | 30 mM | 0.6 mM | 150 mM | — |
| Example 10 | 0.14 mM | 0.1M | 0.0% | 30 mM | 0.4 mM | — | 150 mM |
| Example 11 | 0.14 mM | 0.1M | 0.0% | 30 mM | 0.5 mM | — | 150 mM |
| Example 12 | 0.14 mM | 0.1M | 0.0% | 30 mM | 0.6 mM | — | 150 mM |

<Preparation of Test Pieces>

After impregnating filter paper with each of the reagent impregnating solutions described above, the resulting filter paper was dried at 50° C. for 15 minutes, to obtain test paper. The prepared test paper was cut into a piece of 5 mm×300 mm, and the resulting piece was attached to a PET film of 100 mm×280 mm on which an adhesive agent was attached. The resulting PET film having the test piece attached thereon was cut into a width of 5 mm, to obtain a test piece of 100 mm×5 mm.

<Measurement Method>

In cooperation with 12 volunteers, mouth wash solutions were obtained as test samples by their rinsing the mouth with 3 mL of purified water for 10 seconds and then expectorating the water into a container. On the reagent portion of the test piece, 10 µL of each test sample was dropped, and the change in the reflectance between Minute 1 and Minute 5 at a measurement wavelength of 635 nm and reference wavelength of 760 nm (Δ 4-minute reflectance) was measured for each test paper using a reflectometer. Further, the cariogenic bacterial count in each test sample was measured by plate culture (MSB medium).

Figure 5:
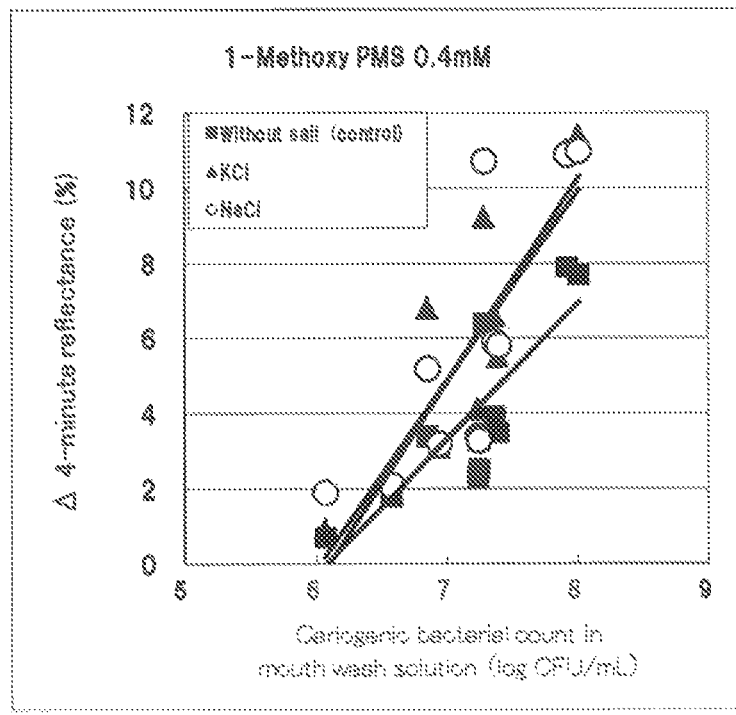
FIG. 5 is a diagram illustrating the correlation between the cariogenic bacterial count in the mouth wash solution and the Δ 4-minute reflectance, which was observed when the 1-methoxy PMS concentration was 0.4 mM and a salt was added or not added.
Figure 6:
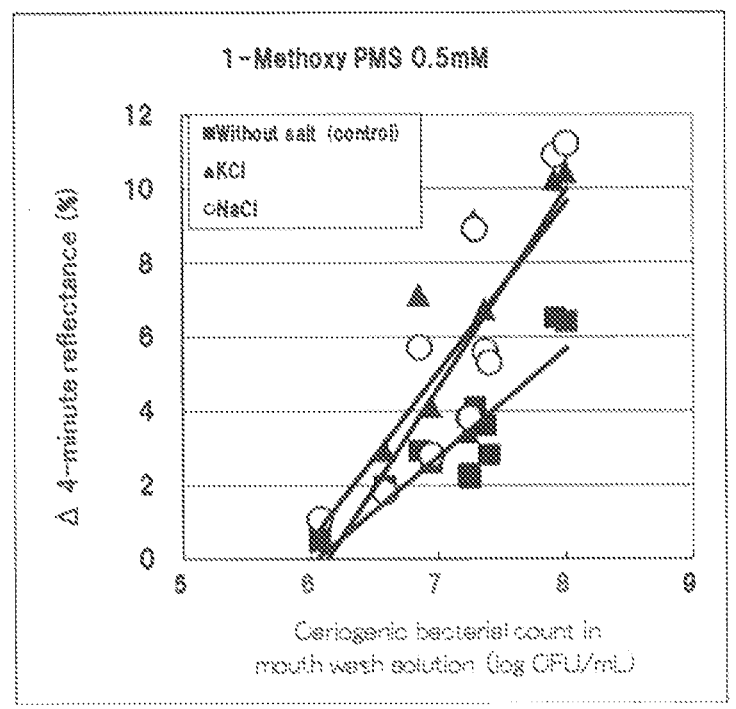
FIG. 6 is a diagram illustrating the correlation between the cariogenic bacterial count in the mouth wash solution and the Δ 4-minute reflectance, which was observed when the 1-methoxy PMS concentration was 0.5 mM and a salt was added or not added.
Figure 7:
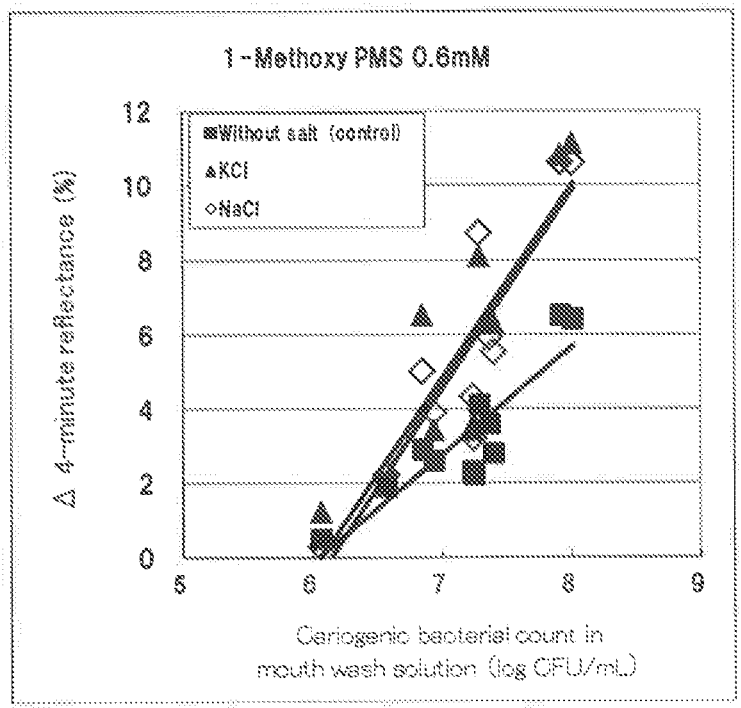
FIG. 7 is a diagram illustrating the correlation between the cariogenic bacterial count in the mouth wash solution and the Δ 4-minute reflectance, which was observed when the 1-methoxy PMS concentration was 0.6 mM and a salt was added or not added.

The results are shown in FIG. 5, FIG. 6, and FIG. 7. As compared to the control group in which only 1-methoxy PMS was added to the basic composition, further addition of KCl or NaCl improved the Δ 4-minute reflectance. Therefore, similarly to the studies using a bacterial suspension of *Streptococcus mutans*, the study using a mouth wash solution showed effectiveness of KCl and NaCl. Further, it was found that, in the groups supplemented with KCl or NaCl, the Δ 4-minute reflectance was similarly high in any of the cases with 1-methoxy PMS at concentrations of 0.4 mM to 0.6 mM. Because of such high Δ 4-minute reflectances, for example, the degree of cariogenic bacterial count in a mouth wash solution can be judged on a 3-point scale.

Experiment Example 4

Study of Effect of Addition of Salts

In the present Experiment Example, the effect of addition of various salts was studied using mouth wash solutions as test samples.

<Formulation>

In 1100 mL of distilled water, 42 mg of sodium resazurin (manufactured by Tokyo Chemical Industry Co., Ltd.), 120 mL of 1 M phosphate buffer (pH 6.0), and 12 g of sucrose (manufactured by Nacalai Tesque) were dissolved to prepare a basic composition, and 1-methoxy PMS and various salts each were added to the prepared basic composition to give the concentrations shown in Table 4, and thus to prepare reagent impregnating solutions.

TABLE 4

Formulation of reagent impregnating solution

| | Pigment Resazurin Manufactured by Tokyo Chemical Industry Co., Ltd. | Buffer Phosphate buffer pH6.0 Manufactured by Nacalai Tesque | Binder PVA Manufactured by Kuraray Co., Ltd. | Carbon source Sucrose Manufactured by Nacalai Tesque | Sensitizer 1-Methoxy PMS Manufactured by Dojindo Tesque | Salts | | | | | | | |
|---|---|---|---|---|---|---|---|---|---|---|---|---|---|
| | | | | | | NaCl Manufactured by Nacalai Tesque | NaBr Manufactured by Nacalai Tesque | KBr Manufactured by Wako Pure Chemical Industries, Ltd. | Na₂CO₃ Manufactured by Nacalai Tesque | MgCl₂ Manufactured by Wako Pure Chemical Industries, Ltd. | Magnesium acetate Manufactured by Nacalai Tesque | Sodium acetate Manufactured by Nacalai Tesque | Sodium tetraborate Manufactured by Nacalai Tesque |
| Example | 0.14 mM | 0.1M Phosphate buffer pH6.0 | 0.0% | 30 mM | 0.4 mM | 50 mM | — | — | — | — | — | — | — |
| Example | 0.14 mM | 0.1M Phosphate buffer pH6.0 | 0.0% | 30 mM | 0.4 mM | — | 100 mM | — | — | — | — | — | — |
| Example | 0.14 mM | 0.1M Phosphate buffer pH6.0 | 0.0% | 30 mM | 0.4 mM | — | — | 100 mM | — | — | — | — | — |
| Example | 0.14 mM | 0.1M Phosphate buffer pH6.0 | 0.0% | 30 mM | 0.4 mM | — | — | — | 100 mM | — | — | — | — |
| Example | 0.14 mM | 0.1M Phosphate buffer pH6.0 | 0.0% | 30 mM | 0.4 mM | — | — | — | — | 100 mM | — | — | — |
| Example | 0.14 mM | 0.1M Phosphate buffer pH6.0 | 0.0% | 30 mM | 0.4 mM | — | — | — | — | — | 100 mM | — | — |
| Example | 0.14 mM | 0.1M Phosphate buffer pH6.0 | 0.0% | 30 mM | 0.4 mM | — | — | — | — | — | — | 100 mM | — |
| Example | 0.14 mM | 0.1M Phosphate buffer pH6.0 | 0.0% | 30 mM | 0.4 mM | — | — | — | — | — | — | — | 100 mM |

<Preparation of Test Pieces>

After impregnating filter paper with each of the reagent impregnating solutions described above, the resulting filter paper was dried at 50° C. for 15 minutes, to obtain test paper. The prepared test paper was cut into a piece of 5 mm×300 mm, and the resulting piece was attached to a PET film of 100 mm×280 mm on which an adhesive agent was attached. The resulting PET film having the test piece attached thereon was cut into a width of 5 mm, to obtain a test piece of 100 mm×5 mm.

<Measurement Method>

In cooperation with 12 volunteers, mouth wash solutions were obtained as test samples by their rinsing the mouth with 3 mL of purified water for 10 seconds and then expectorating the water into a container. On the reagent portion of the test piece, 10 μL of each test sample was dropped, and the change in the reflectance between Minute 1 and Minute 5 at a measurement wavelength of 635 nm and reference wavelength of 760 nm (Δ 4-minute reflectance) was measured for each test paper using a reflectometer.

Figure 8:
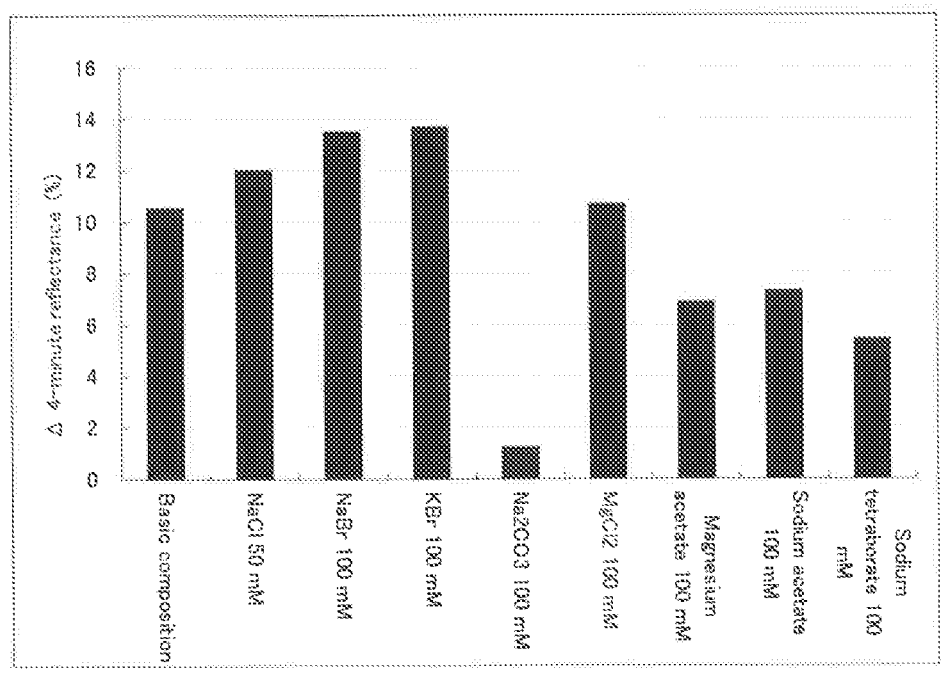
FIG. 8 is a diagram illustrating the effect of each salt on the Δ 4-minute reflectance.

The results are shown in Table 5 and FIG. 8. As compared to the control group in which only 1-methoxy PMS was added to the basic composition, further addition of KBr or NaBr improved the Δ 4-minute reflectance.

TABLE 5

| | Concentration | Δ 4-Minute |
|---|---|---|
| Basic composition | — | 10.5 |
| NaCl 50 mM | 50 mM | 12.0 |
| NaBr 100 mM | 100 mM | 13.5 |
| KBr 100 mM | 100 mM | 13.7 |
| Na₂CO₃ 100 mM | 100 mM | 1.2 |
| MgCl₂ 100 mM | 100 mM | 10.7 |
| Magnesium acetate 100 mM | 100 mM | 6.9 |
| Sodium acetate 100 mM | 100 mM | 7.3 |
| Sodium tetraborate 100 mM | 100 mM | 5.4 |

INDUSTRIAL APPLICABILITY

By the present invention, a color change of an oxidation-reduction indicator can be clearly measured. Thus, by the present invention, the cariogenic bacterial count can be measured at room temperature in a short time. Therefore, by the present invention, in clinical sites such as dental clinics, many samples can be processed without use of facilities such as an incubator, and the cariogenic bacterial count can be measured simply and rapidly. The measurement result can be preferably used for, for example, judgment of the caries risk of the subject. Thus, the present invention is effective for prevention of caries and the like.

DESCRIPTION OF SYMBOLS

1. Test Piece
10. Support carrier
11. Absorption carrier

The invention claimed is:

1. A method for measuring cariogenic bacterial count in a test sample comprising cariogenic bacteria using a color change of an oxidation-reduction indicator, the method comprising the steps of:
   reacting a test reagent with the test sample and measuring the resulting color change by a reflectometer, wherein the test reagent comprises:
   resazurin as an oxidation-reduction indicator;
   an oxidation-reduction promoter selected from the group consisting of 1-methoxy-5-methylphenazinium methyl sulfate, phenazinium methyl sulfate and phenazine ethosulfate; and
   a halogen salt selected from the group consisting of sodium chloride, potassium chloride, sodium bromide and potassium bromide present at a concentration range of from 50 to 200 mM, wherein the method measures the cariogenic bacterial count based on the degree of the color change of said oxidation-reduction indicator.

2. The method according to claim 1, wherein the measurement is carried out on a test piece comprising a support carrier and an absorption carrier carried by the support carrier, wherein the absorption carrier holds the test reagent.

* * * * *